(12) United States Patent
Fowler

(10) Patent No.: US 6,607,494 B1
(45) Date of Patent: Aug. 19, 2003

(54) MUCOSAL SAMPLER

(75) Inventor: Robert Stuart Fowler, Scottsdale, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 18 days.

(21) Appl. No.: 09/766,866

(22) Filed: Jan. 19, 2001

Related U.S. Application Data

(60) Provisional application No. 60/177,106, filed on Jan. 20, 2000.

(51) Int. Cl.[7] ............................................. A61B 10/00
(52) U.S. Cl. ....................................................... 600/570
(58) Field of Search ................................. 600/564, 569, 600/570, 572

(56) References Cited

U.S. PATENT DOCUMENTS

| | | | | |
|---|---|---|---|---|
| 4,757,826 A | * | 7/1988 | Abdulhay | .................. 600/570 |
| 5,022,408 A | * | 6/1991 | Mohajer | ..................... 600/569 |
| 5,121,752 A | * | 6/1992 | Canna | ......................... 600/572 |
| 5,722,423 A | * | 3/1998 | Lind et al. | .................. 600/569 |

* cited by examiner

*Primary Examiner*—Kevin Shaver
*Assistant Examiner*—Pamela Wingood
(74) *Attorney, Agent, or Firm*—Gregory F. Cotterell

(57) ABSTRACT

A cytology cell sampler for use in collecting mucosal cell samples from a human comprising a handle and a head portion. The handle is grasped by the operator and the head portion is then abutted a patient's mucosal surface for sample collection. The head portion has a first plate and a plurality of secondary plates with the first plate attached to the handle opposite the end grasped by the operator. The first plate has a longitudinal axis generally along a longitudinal axis of the handle, and the plurality of secondary plates project from the first plate generally perpendicular to the longitudinal axis of the first plate. There is at least one collection space between the plurality of secondary plates. Each secondary plate has a shaped free edge for contacting the mucosal surface of the human, collecting a sample between the plurality of secondary plates by scraping the mucosal surface with the shaped free edges.

12 Claims, 4 Drawing Sheets

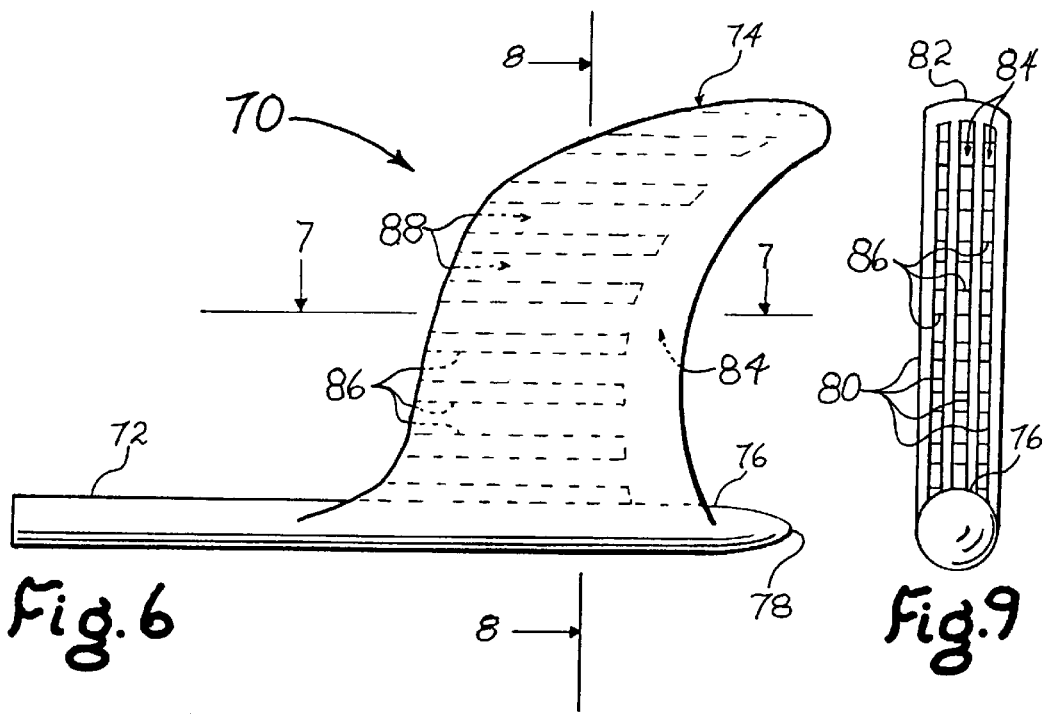
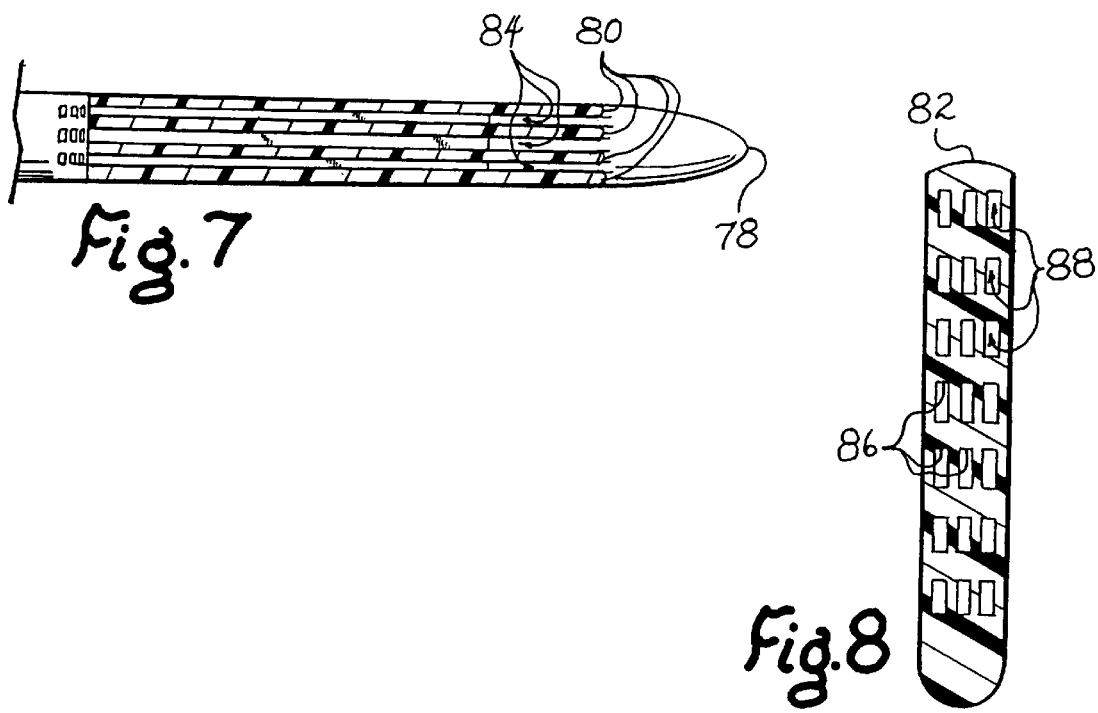

MUCOSAL SAMPLER

This application claims benefit of Provisional No. 60/177,106 filed Jan. 20, 2000.

FIELD OF THE INVENTION

The present invention discloses a device for mucosal cell and tissue collection, in particular, for an improved device for performing cytological smears and endocervical curettage useful in the detection and diagnosis of cancer, and more particular, an improved device for collecting cytological smears and endocervical tissue for the detection of uterine cervical dysplasia and cancer.

BACKGROUND OF THE PRESENT INVENTION

Uterine cervical cancer poses a significant medical risk in the female population. The commonest test for screening a patient for cervical dysplasia or cancer of the cervix consists of obtaining a sample of endocervical and ectocervical cells lining the cervix and performing the Papanicalaou test on the sample, the so called Pap test. A complimentary test, known as the endocervical curettage is used to collect endocervical tissue for pathological analysis.

In its own right, the Pap test is fairly simple to perform and reasonably sensitive in providing accurate and reliable results. A recent advancement has improved the quality of cellular deposit by immersion of samplers into cytology fluid and processing by a monolayer technique. Difficulty persists in achieving an adequate collection and deposition of cells into the cytology fluid for processing and analysis. The traditional method uses a shaped wood spatula, the shaped edge being scraped over the mucosal surface, for example, the mucosa of the ectocervix and opening of the endocervical canal. Unfortunately, this method commonly results in a specimen lacking endocervical cells and occasionally insufficient squamous cells, as well.

Over the years, numerous improvements for cell samplers have been offered. Examples of such improvements include modifying the surface of the wood spatula or making the spatula out of plastic. A sampler with multiple surfaces in concentric rings has been proposed. The most dramatic improvement occurred with the introduction of brushes that provide many small fibers that can be inserted into the endocervix and dragged across the surface of the mucosa. Some physicians are using the latter devices in lieu of performing the traditional endocervical curettage with small metal curettes.

Drawbacks still exist with these devices despite their enhanced surfaces and edges. Inadequate sample cellularity in general, or, more frequently, inadequate endocervical cell/tissue collection or inability of the devices to release the sample into the cytology fluid.

What is needed is a device that is capable of safely and consistently obtaining endocervical glandular cells and or tissue, and ectocervical squamous cells, and readily releasing the cellular collection into cytology fluid.

SUMMARY OF THE INVENTION

The present invention is an improved device for obtaining mucosal cell and tissue samples by passing the device of the present invention over the surface of the mucosa. The present invention, as depicted, for example, in FIGS. 1–3, discloses a device having a handle attached to a first plate. The first plate has a first side and a second side and defines a first plane, from which extend a plurality of secondary plates from both a first side and a second side of the first plate. This depicts the symmetry of structure in relation to the first plate that is possible with the present invention. The secondary plates each define planes that are perpendicular to the plane of the first plate and are oriented generally parallel to each other forming a plurality of rows of secondary plates extending from each surface of the first plate. The present invention anticipates that the overall outer shape of the device depends on the overall width of the first plate and height of the secondary plate from the surface of the first plate, the geometry and thickness of the secondary plates, and the shape of the edge of each of the secondary plates. In addition, the secondary plates present surfaces that are parallel to the surface of the next plate. The secondary plates are sufficiently close to be suitable for capillary flow of fluids into and through the interspaces between each secondary plate. Good capillary action can be expected when the inter-space is about one to two millimeters or less. The present invention relies on this capillary action to wick away cell laden fluids from the mucosal surface deep into the interspaces between the secondary plates. The outer edges of the secondary plates may also be contoured with serrations, bevels, or microfilaments at the edges of the secondary plates.

Additional examples of patterns for secondary plates are shown in the various Figures. As depicted in FIG. 5, for example, the present invention discloses a device similar to the embodiments of FIGS. 1–4, but with several tiers of secondary plates. Each secondary plate has a tapered shape. In this embodiment, the taper is roughly two to one in relationship to the distance between the adjacent secondary plates. Other ratios may be used. In addition, the spaces between the secondary plates are even in dimension from proximal to distal. The added advantage of having a tapered secondary plate is to provide variable stiffness to the secondary plates, enhancing the curetting action of the edges of the secondary plates, as well as, enhancing the movement of the cell sample into the spaces between the secondary plates.

The present invention also anticipates that the spaces between the secondary plates may not be parallel, nor may they be so narrow as to provide for capillary action. In addition, these spaces may use geometric shapes and have widths as great as 2 to 4 mm, or larger, and act more as reservoirs for the collected cellular/fluid material as it is scraped free from the mucosal surface.

Another embodiment of the present invention, depicted in FIGS. 6–9, discloses a device having a handle attached to at least two secondary plates. The area of attachment of the secondary plates to the handle serves the function of acting as the first plate. This embodiment serves to depict the asymmetry of structure in relation to the first plate that is possible with the present invention, demonstrating the adaptability of the present invention for use over different mucosal surfaces. The at least two plates are oriented parallel to each other and present a large surface area. The at least two plates are spaced close enough to each other to be suitable for capillary flow of fluids into the space between the at least two plates. In addition, in this embodiment, the at least two plates are spaced apart from each other by a plurality of ribs. The ribs do not extend completely across the breadth of the at least two plates providing for channels between the at least two plates through which air can be displaced to the upper edge of the device as cell laden fluid is drawn into the primary reservoir between the at least two plates along the lower edge of the device.

Both of these embodiments may be attached at opposite ends of the same handle. By way of example, the first embodiment is useful for obtaining glandular cell samples from the lining of the endocervical canal. The second embodiment is useful for obtaining squamous cell samples from the outer surface of the cervix, the ectocervix. When combined on the same handle, the device of the present invention becomes a sampling device useful for obtaining samples of cells from within and without the cervix without having to use multiple devices.

In operation, the handle of the first embodiment is used by an operator to orient the plane of the first plate parallel to the longitudinal axis of the endocervical canal with the planes of each of the secondary plates at right angles to the plane of the first plate, but also parallel to the longitudinal axis of the endocervical canal. The outer profile of the secondary plates, when viewed end on, is circular in cross-section and the plates taper toward the tip at the end of the first plate that is away from the end attached to the handled. When the device is aligned with the endocervical canal, the handle is used to insert the head of the device into the endocervical canal and rotate the head around the axis of the endocervical canal. As the head rotates, cell or tissue samples are collected between the secondary plates and if close enough to each other, held there by capillary action. Alternatively, the cell or tissue samples collect within the reservoir space between the secondary plates. Repeated in and out movement is not necessary, thus diminishing the likelihood of mechanically introducing unwanted contaminants from the vaginal vault into the uterus.

When sampling is completed, the device is withdrawn from the endocervical canal and vaginal vault and the head of the device may be used to either create a smear directly onto a slide or, preferably, dipped into cytology fluid and swished to remove the cells from between the secondary plates or swished in preservative to deposit the tissue. The sample is then ready for the physician, a pathologist, cytologist, or lab technician to prepare for histologic study.

The second embodiment is similarly operated. The handle is used by the operator to align the extended tip of the device with the external os of the cervix. The tip is then placed into the cervical os until the leading edge of the at least two plates contacts the outer surface of the cervical os. The device is then rotated and cell samples are collected between the at least two plates comprising the primary reservoir. The channels provide for release of air pressure as the primary reservoir fills. If needed, the channel spaces may also collect cell sample overflow from the primary reservoir.

When sampling is completed, the device is withdrawn from the vaginal vault and the head of the device is swished into cytology fluid to remove the cell samples from between secondary plates. The channels provide for flow of the cytology fluid through the head of the device between the at least two plates to empty the primary reservoir of cell samples. The sample is then ready for the physician or lab technician to prepare for histologic study.

A number of materials are suitable for use in the various embodiments of the present invention and include, without limitation, synthetic plastics and natural and synthetic rubber compounds. There are a number of plastics known in the art that are useful in this capacity. Examples are poly-vinyl-chloride, polypropylene, polyethylene, polystyrene, polyurethane, polytetrafluoroethylene, and their copolymers. Preferably the plastic is biocompatible, as well as, sterilizable using standard sterilization techniques known in the medical arts. Alternatively, the devices of the present invention may be manufactured in metal or ceramic materials. Useful metals are iron, steel, stainless steel, chromium, tungsten, vanadium, molybdenum, nickel, aluminum, titanium, and alloys of these metals.

The above and other objects and advantages of the present invention become more readily apparent when reference is made to the following detailed description taken in conjunction with the accompanying drawings. The following descriptions are in no way intended to limit the scope of the present invention.

BRIEF DESCRIPTION OF THE DRAWINGS

FIG. 6 is a side elevational view of yet an additional alternative embodiment of the present invention;

FIG. 7 is a cross-sectional view taken at line 7–7 of FIG. 6;

FIG. 8 is a cross-sectional view taken at line 8–8 of FIG. 6: and

FIG. 9 is an end-on view of the embodiment depicted in FIG. 6.

DETAILED DESCRIPTION OF THE INVENTION

Figure 1:
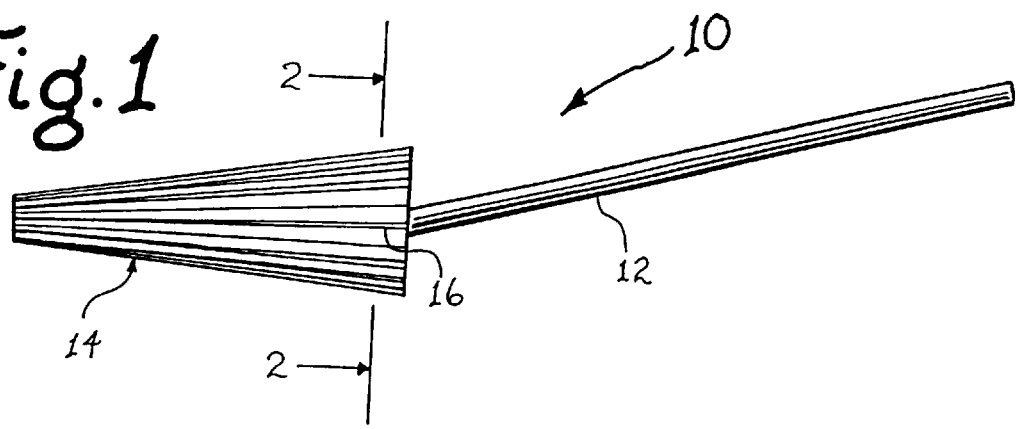
FIG. 1 is a side elevational view of an embodiment of the present invention.
Figure 2:
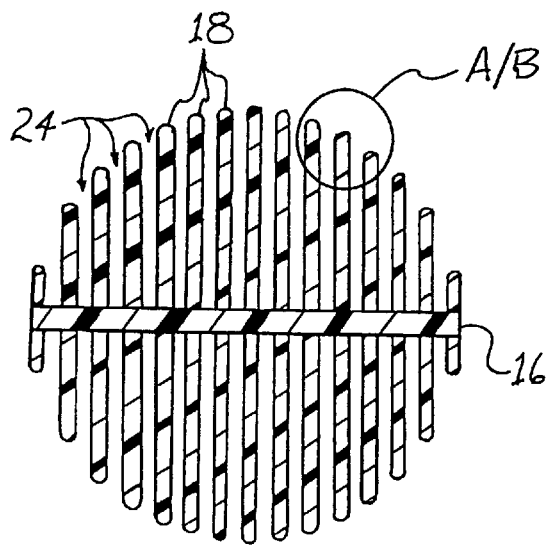
FIG. 2 is a cross-sectional view taken at line 2–2 of FIG. 1.
Figure 2A:
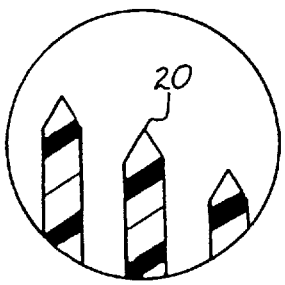
FIG. 2A is a magnified cross-sectional view of the area depicted at A/B of FIG. 2 and depicts an alternative embodiment of the present invention.
Figure 2B:
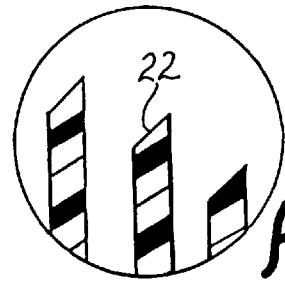
FIG. 2B is a magnified cross-sectional view of the area depicted at A/B of FIG. 2 and depicts another alternative embodiment of the present invention.
Figure 3:
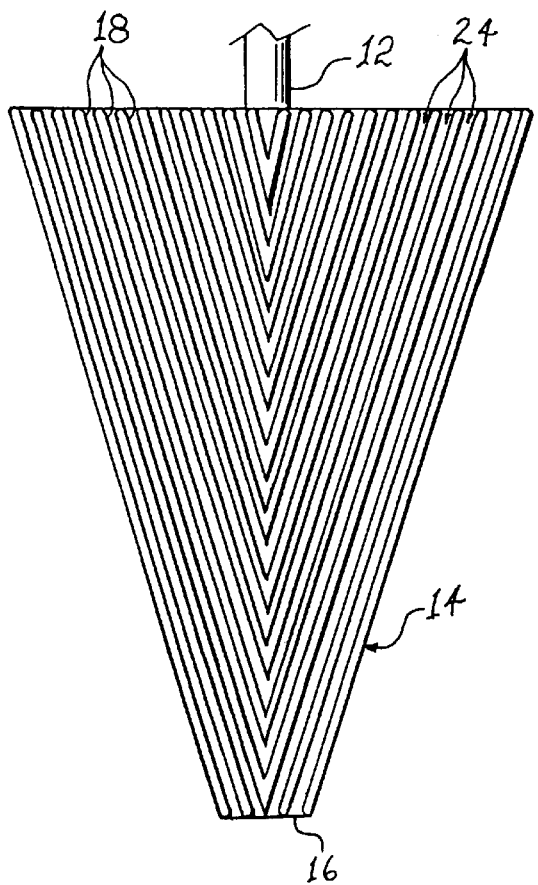
FIG. 3 is a top plan view of the embodiment depicted in FIG. 1.
Figure 5:
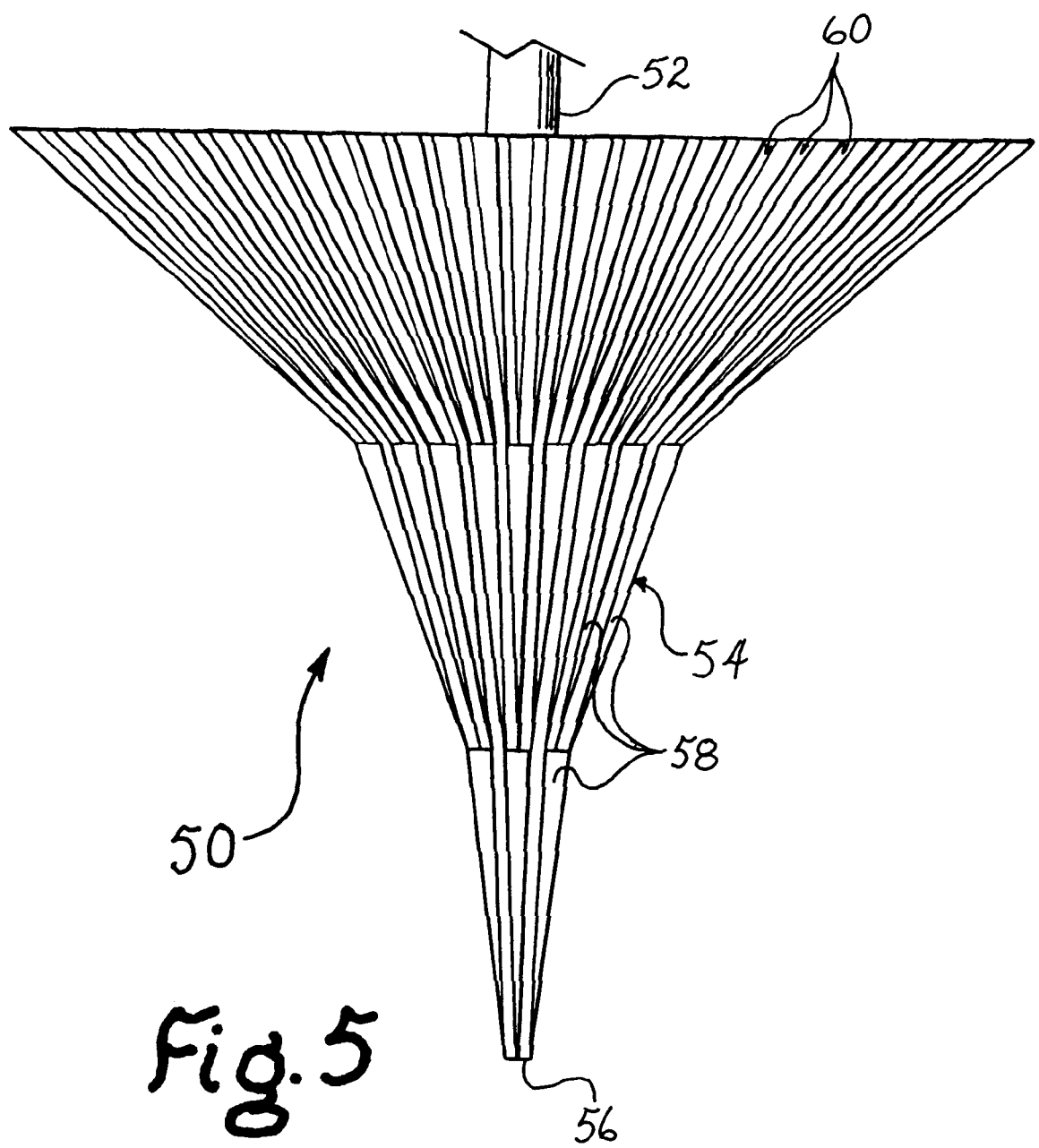
FIG. 5 is a top plan view of still another additional alternative embodiment of the present invention.

Referring to FIGS. 1 through 3, wherein like numbers depict like components through out the various Figures, there is depicted a cytology cell sampler device 10 comprising a handle 12 and a sampler head 14. Sampler head 14 includes a first plate 16 and a plurality of secondary plates 18. Secondary plates 18 include free edges that are shapeable, as depicted by edges 20 and edges 22. Additionally, the device profile may be altered by further shaping the edges of secondary plates 18 in the longitudinal direction of sampler head 14. One example of this concept is represented by FIG. 5.

Secondary plates 18 are parallel to each other and separated by spaces 24. In FIG. 3, secondary plates 18 are parallel one plate to the next. The overall pattern of secondary plates 18 is wedge shaped, as depicted in FIG. 3, where each half is the mirror image of the other half. Additionally, secondary plates 18 are depicted as projecting from both sides of first plate 16, as is shown in FIGS. 1 and 2. As is evident below, the present invention anticipates that there does not need to be symmetry of the secondary plates to both sides of the first plate.

It is within spaces 24 that the cellular laden fluid scraped free of the mucosal surface by the edges of secondary plates 18 is collected. When spaces 24 are sufficiently narrow, there may actually be a capillary action that further enhances the wicking effect, pulling cell-laden fluid into spaces 24, improving the collection process.

As depicted in FIG. 1, handle 12 is oriented at an angle to the longitudinal axis of sampler head 14. Handle 12 may project 180° straight out from sampler head 14, or as depicted, at an angle less than 180°, but preferably at an obtuse angle. Such an angle might be in the range of about 179° to about 135°.

Cell sampler device 10 may be manufactured as a single, integral unit, easily accomplished using injection mold techniques for plastics. However, this does not preclude manufacturing the device of the present invention as a single integral unit out of metals or ceramics. Alternatively, the present invention anticipates that handle 12 may be detachable from sampler head 14. This may be desirable for those circumstances where the operator may wish to place the entire sampler head into a jar of preservative fluid and remove the handle. Such technique ensures that the entire sample is sent to the pathology laboratory where the sampler head may be examined directly by the cytologist to remove any adherent sample material. Detachable devices of the present invention may have sampler heads and handles made from similar or dissimilar materials.

Figure 4:
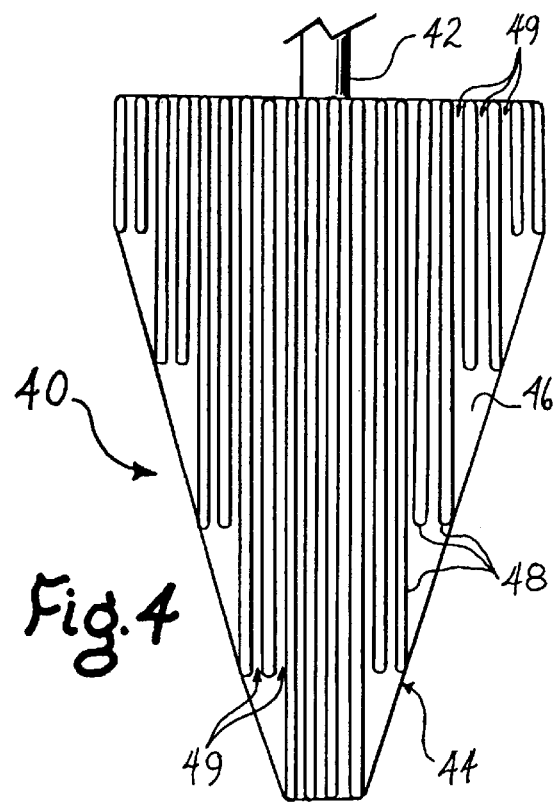
FIG. 4 is a top plan view of another additional alternative embodiment of the present invention.

FIG. 4 depicts an alternative embodiment of the present invention as a cytology cell sampler device 40 comprising a handle 42 and a sampler head 44. Sampler head 44 includes a first plate 46 and a plurality of secondary plates 48. In this embodiment, all of secondary plates 48 are parallel to each other. Truncating sampler head 44 is achieved by using secondary plates of diminishing length the further out from center the secondary plate resides on first plate 46. As with the previous embodiment, this embodiment may include a set of secondary plates on the other side of first plate 46. The plurality of secondary plates 48 are separated from each other by spaces 49. Sampler head 44 may have a similar profile to sampler head 14 of FIG. 1, or some other profile depending on the heights of the secondary plates.

FIG. 5 depicts another alternative embodiment of the present invention as a cytology cell sampler device 50 comprising a handle 52 and a sampler head 54. Sampler head 54 includes a first plate 56 and a plurality of secondary plates 58. In this embodiment, secondary plates 58 are not parallel to each other, rather secondary plates 58 are wedge-shaped fore to aft. This results in a differential widening of sampler head 54 while providing for secondary plates 58 to be separated by spaces 60 that still have uniform width. As with the previous embodiments, this embodiment may include a set of secondary plates on the other side of first plate 46 and may have a similar profile to sampler head 14 of FIG. 1, or some other profile depending on the heights of the secondary plates.

FIGS. 6–9 depict another alternative embodiment of the present invention as a cytology cell sampler device 70 comprising a handle 72 and a sampler head 74. Sampler head 74 includes a first plate 76 ending in tip 78 and a plurality of secondary plates 80 extending from only one surface of first plate 76 and capped by a cross plate 82. Each secondary plate 80 is separated from the others by spaces 84. As alluded to above, this embodiment demonstrates how the outer edges of the secondary plates may be shaped to achieve a different profile, and thus a different working edge. Additionally, the symmetry of secondary plates above and below the first plate is also not retained. However the overall structure and function remains the same as before. The edges of secondary plates 80 are used to scrape the mucosal surface and cells and fluid are then drawn into spaces 84 between secondary plates 80. Cross plate 82 is optional and serves the purpose of stabilizing the free ends of secondary plates 80. In addition, there is a plurality of bridging bars 86 through sampler head 74 that bridge between the various secondary plates 80. These bridging bars 86 are optional and provide additional structural stability. Bridging bars 86 divide spaces 84 into a plurality of vents 88 so that as cellular fluid is scraped and drawn into spaces 84, displaced air may escape through vents 88.

Lastly, first plate 76 is not required to be structurally flat. The present invention recognizes the flexibility for adopting shapes that best suit the needs designed for the device. In the embodiment depicted in FIGS. 6–9, cell sampler device 70 is adapted to have a first plate 76 with a tip 78 that fits within the cervical os. The tip is round to provide for a smooth rotation of device 70 around the axis of the cervical canal at the cervical os.

In operation, and as an example for obtaining a sample of cells and fluid from the endocervical canal, handle 12 is used by an operator to orient the plane of first plate 16 parallel to the longitudinal axis of the endocervical canal with the planes of each of secondary plates 18 also parallel to the longitudinal axis of the endocervical canal. The outer profile of secondary plates 18, when viewed end on, is circular in cross-section and edges 20 of secondary plates 18 taper toward the tip at the end of first plate 16 away from handle 12. After sampler device 10 is aligned with the endocervical canal, sampler head 14 is inserted into the endocervical canal and rotated around the axis of the endocervical canal. As sampler head 14 rotates, cell or tissue samples are scraped free by edges 20 and collected between secondary plates 18 in spaces 24. If secondary end plates 18 are close enough to each other, the cellular fluid is held there by capillary action. Alternatively, the cell or tissue samples collect within the reservoir space between the secondary plates. Repeated in and out movement is not necessary, thus diminishing the likelihood of mechanically introducing unwanted contaminants from the vaginal vault into the uterus.

When sampling is completed, sampler device 10 is withdrawn from the endocervical canal and vaginal vault and sampler head 14 of the device may be used to either create a smear directly onto a slide or, preferably, dipped into cytology fluid and swished to remove the cells from between the secondary plates or swished in preservative to deposit the tissue.

The embodiment depicted in FIGS. 6–9 is similarly operated. Handle 72 is used by the operator to align tip 78 of sampler device 70 with the external os of the cervix. Tip 78 is then placed into the cervical os until the leading edges of secondary plates 80 contact the outer surface of the cervix. Sampler device 70 is then rotated and cell samples are collected in spaces 84 between secondary plates 80 comprising the primary reservoir. Vents 88 provide for release of air pressure as the primary reservoir fills. If needed, vents 88 may also collect cell sample overflow from the primary reservoir.

When sampling is completed, sampler device 70 is withdrawn from the vaginal vault and the head of the device is swished into cytology fluid to remove the cell samples from between secondary plates 80. Vents 88 provide for flow of the cytology fluid through sampler head 74 between secondary plates 80 to empty the primary reservoir of cell samples.

The foregoing description is considered as illustrative only of the principles of the invention, since numerous modifications and changes will readily occur to those skilled in the art. Consequently, it is not desirable to limit the invention to the exact construction and operation shown and described herein. Accordingly, all suitable modification and equivalents may be resorted to, falling within the scope of the present invention.

I claim:

1. A mucosal sampler for use in collecting mucosal cell or tissue samples from a human, the mucosal sampler comprising:

a handle for grasping at a first end, having a longitudinal handle axis, and a head portion having a first plate and a plurality of secondary plates, the first plate attached to the handle at a second end of the handle and having a longitudinal plate axis, and the plurality of secondary plates projecting from the first plate generally perpendicular to the longitudinal axis of the first plate, the plurality of secondary plates arranged substantially parallel to each other spaced side by side in a perpendicular plane with respect to the longitudinal axis, and having at least one collection space between the plurality of secondary plates, and each secondary plate having a shaped free edge for contacting the mucosal cells or tissue of the human, the cell or tissue sample being collected in the at least one space between the plurality of secondary plates.

2. The invention of claim 1 in which the handle and head portion comprise a polymer.

3. The invention of claim 2 in which the polymer comprises a polymer selected from a list of polymers consisting of: elastomeric silicone, polyethylene, polypropylene, polyester, polyurethane, poly(vinyl chloride), polyisobutylene, polychloroprene, polybutadiene, and copolymers of this list.

4. The invention of claim 1 in which the handle and head portion comprise a metal.

5. The invention of claim 4 in which the metal comprises a metal selected from a list of metals consisting of: iron, steel, stainless steel, chromium, tungsten, vanadium, molybdenum, nickel, aluminum, titanium, and alloys of metals of this list.

6. The invention of claim 3 in which the handle and the head portion are integral in construction.

7. The invention of claim 1 in which the handle and the head portion are constructed separately and joined together.

8. The invention of claim 7 in which the handle comprises a metal and the head portion comprises a polymer and the head is attachable to the handle.

9. The invention of claim 8 in which in which the polymer comprises a polymer selected from a list of polymers consisting of: elastomeric silicone, polyethylene, polypropylene, polyester, polyurethane, poly(vinyl chloride), polyisobutylene, polychloroprene, polybutadiene, and copolymers of this list.

10. The invention of claim 8 in which the metal comprises a metal selected from a list of metals consisting of: iron, steel, stainless steel, chromium, tungsten, vanadium, molybdenum, nickel, aluminum, titanium, and alloys of metals of this list.

11. The invention of claim 1 in which the longitudinal handle axis forms an obtuse angle with the longitudinal plate axis.

12. The invention of claim 11 in which the obtuse angle is from about 179° to about 135°.

* * * * *